United States Patent [19]

Suga

[11] 4,049,351
[45] Sept. 20, 1977

[54] CONTACT MEANS FOR A WEATHER RESISTANCE AND SOLAR RADIATION TESTER

[76] Inventor: Shigeru Suga, Yoyogi 5-20-2, Shibuya, Tokyo, Japan

[21] Appl. No.: 671,701

[22] Filed: Mar. 29, 1976

[51] Int. Cl.$^2$ .................... G01N 21/24; H01R 39/02; H01R 39/08
[52] U.S. Cl. ................................ 356/72; 339/5 R; 356/244
[58] Field of Search ........................ 356/72, 244, 256; 339/5 R, 5 L, 5 M, 5 P, 8 R, 8 L

[56] References Cited

U.S. PATENT DOCUMENTS

| 1,460,037 | 6/1923 | Pierson | 339/8 L |
| 3,889,531 | 6/1975 | Suga | 356/256 |

FOREIGN PATENT DOCUMENTS

| 22,138 | 10/1912 | United Kingdom | 339/8 R |

Primary Examiner—John K. Corbin
Assistant Examiner—Wm. H. Punter
Attorney, Agent, or Firm—Wenderoth, Lind & Ponack

[57] ABSTRACT

Improved contact means for use in a weather resistance and solar radiation tester having a specimen rotating frame having leads extending through the shaft and a meter for indicating the amount of light received by the light receiving element. The improved contact means is for electrically connecting the leads to the meter, and has a rotating shaft connected to the shaft for the specimen rotating frame, upper and lower cases surrounding the rotating shaft and in which the rotating shaft is rotatably journaled and defining two separate compartments spaced along the rotating shaft and sealed from each other, the cases being of electrically insulating material. A metal ring is fixed in the bottom of each case and a lead extends from each ring out through the respective case for connection to the meter. A plate spring in each compartment is fixed to the rotating shaft, and contact pieces on the ends of the plate spring in each compartment are held in sliding contact with the metal ring therein. The leads extend through the rotating shaft into the compartments and are electrically connected to the contact pieces therein. An electrically insulating liquid is provided in each compartment covering the rings and contact pieces therein, whereby deterioration of the resistance value of the contact means is avoided by elimination of the contamination due to contact wear.

4 Claims, 7 Drawing Figures

CONTACT MEANS FOR A WEATHER RESISTANCE AND SOLAR RADIATION TESTER

This invention relates to a weather resistance and solar radiation resistance tester for continuously measuring light engery falling on the surface of a specimen from a light source such as a carbon arc lamp or a xenon lamp serving as a source of artificial solar radiation and, more particularly relates to a contact means for electrically connecting a light receiving section on the specimen surface and a separately provided measuring mechanism.

BACKGROUND OF THE INVENTION AND PRIOR ART

In the usual weather resistance and solar radiation resistance tester, a specimen supported on a specimen rotating frame is exposed to light energy under suitably selected temperature and relative humidity conditions as it is revolved around a light source such as a carbon arc lamp or a xenon lamp disposed at the center of the rotating frame for testing the specimen for light fastness and weather resistance. In order to be able to measure or adjust the light energy incident on the sample, it has been the usual practice to provide a light receiving element such as a photoelectric tube or photomal (photoelectric multiplier tube) on the surface of the specimen and connect it to a meter outside the tester. In such an arrangement, leads from the light receiving element are led through a pipe constituting the shaft of the sample rotating frame and are connected at the lower end to contact means constituted by a slip ring for connection to the meter so that they are not twisted during the rotation of the rotating frame.

The prior art contact means of this type has a structure consisting of a disc or a rotor of a similar shape made of an insulating material, on which a metal ring and metal or carbonaceous slide contacts are provided, and the contact portion thereof is the so-called dry type, that is, it is exposed to air.

The light receiving section consisting of the photoelectric tube or photomal has a high input impedance (i.e. input resistance) which is required for its performance, and even a slight reduction of the insulation resistance in the contact section leads to errors in the measurement. Therefore, the prior art contact means which is exposed to air must always be kept clean because contamination of the insulating material between the two electrodes or between an electrode and ground due to contact wear causes a reduction of the insulation resistance. For example, a resistance which is greater than 2,000 MΩ when the contact means is new is sometimes reduced to about 20 MΩ due to contamination. In this case, current flows in the photoelectric tube even if it does not receive light energy, that is, the tube indicates an apparent light reception condition. Also, since the contact means is exposed to air, the resistance thereof is likely to be reduced due to the effect of moisture.

OBJECT AND BRIEF SUMMARY OF THE INVENTION

It is an object of the present invention to provide a contact means for a weather resistance and solar radiation tesing device which overcomes the above drawbacks. To this end, the present invention provides a contact construction consisting of two compartments electrically isolated from each other and each accommodating a contact and being filled with an insulating oil, such as fluid paraffin, to prevent exposure of the contact to air and also to prevent corrosion of the contact section, thus eliminating the reduction of the electric resistance due to contamination as a result of contact wear, thereby to permit accurate measurement with the apparatus over a long period of use.

BRIEF DESCRIPTION OF THE DRAWING

An embodiment of the invention will now be described with reference to the accompanying drawing, in which:

FIG. 4 is a block diagram showing an example of a light measuring system using the contact means of the invention;

DETAILED DESCRIPTION OF THE INVENTION

Figure 1:
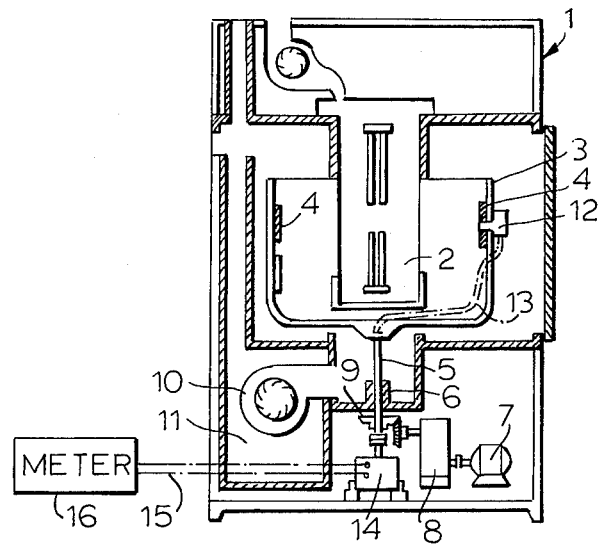
FIG. 1 is a schematic sectional elevation view showing the construction of a weather resistance and solar radiation resistance tester incorporating a contact means according to the invention.

Referring to FIG. 1, designated at 1 is a weather resistance and solar radiation resistance tester having a carbon lamp 2 as a light source disposed within the tester. A specimen rotating frame 3 with sample 4 attached in a row on the inner wall thereof is rotatable around lamp 2. A motor 7 drives a rotating shaft 5 supporting the rotating frame 3 through bevel gears 9 and a transmission 8. A fan 10 is provided in the device for supplying air at a desired temperature and relative humidity from within a space 11 to the interior of the test chamber.

A light receiving element 12 is mounted on rotating frame 3 for measuring the light energy falling thereon. It consists of a photoelectric tube or a photomal, and has leads 13 extending through a pipe constituting the shaft 5 and connected to a contact means 14 according to the invention. Leads 15 extend from the contact means to a meter 16.

Figure 2:
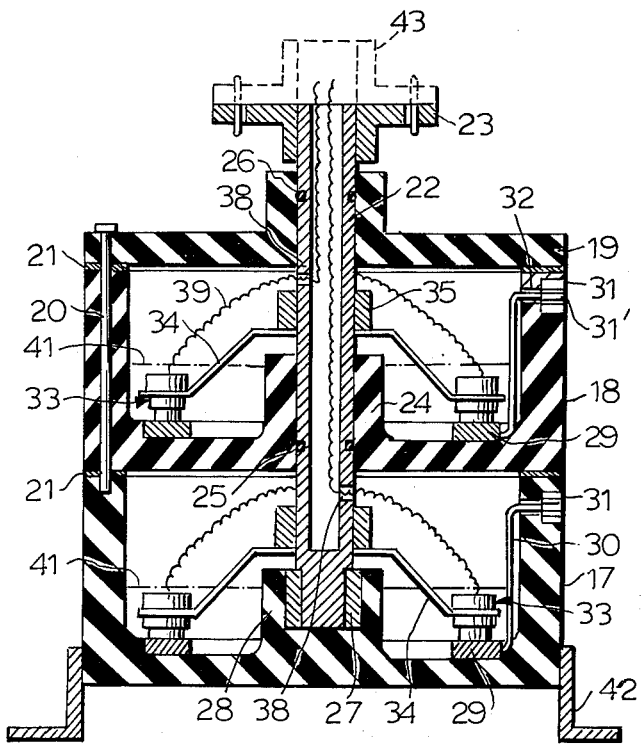
FIG. 2 is an enlarged sectional view showing the construction of the contact means according to the invention.

FIG. 2 illustrates the internal construction of the contact means 14 according to the invention. The contact means has an open top lower case 17, an open top upper case 18 covering the top of the lower case 17, and a top lid 19 covering the top of the upper case 18. These parts are all made of a high electric resistance material (for instance, ethylene tetrafluoride marketed under the trade name "Teflon") and define upper and lower compartments. The upper and lower cases and top lid are secured together by bolts 20, and packings 21 are secured in sealing relationship between the top lid 19 and upper case 18, and also between the upper and lower cases 18 and 17.

A rotatable shaft 22 having a flange 23 secured to the top thereof is connected to the rotating shaft 5 of the tester and extends through the lid 19 and upper case 18 and into the lower case 17. In order to prevent flow of oil between the two compartments, an O-ring 25 is fitted in an annular groove in an portion of the shaft 22 extending through a bearing portion 24 of the case 18. A similar O-ring 26 is also provided within a bearing portion of the top lid 19. The lower end portion of the shaft is journaled in a third bearing 27 in lower case 17, which is made of a material different from that of the shaft 22 (for instance, copper, brass or the like) to provide for smooth rotation of the shaft, and is bonded or secured to a bearing portion 28 of the lower case 17. Metal rings 29 are provided in the bottoms of cases 17 and 18 and to the peripheral portion of which respective leads 30 are welded or soldered. The rings 29 are secured to the bottom of the respective lower and upper cases 17 and 18 by means of adhesive or screws (in the illustrated case they are secured by adhesive).

Each lead from each ring is passed through a hole 32 formed in an upper portion of each case and is connected to a terminal piece 31, the holes 32 being sealed with an adhesive material and the terminal pieces 31 secured to the cases 17 and 18 after being connected to leads 30. Leads 15 from the meter are connected to each of the terminal pieces 31 by suitable means such as screwing or soldering.

Contact sections 33 are provided for each metal ring, each of which is secured by a plate spring 34 to a boss 35 which is, in turn, secured by screws to the rotating shaft 22 with the position of securement being adjusted so that the contact section 33 can slide on the ring 29 with an adequate pressure to ensure proper transmission of the photocurrent from element 12.

Figure 4:
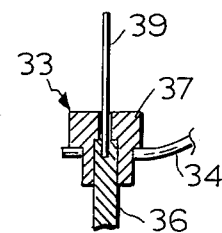
FIG. 4 is a sectional view, on an enlarged scale, of a part of FIGS. 2 and 3.

The structure of the contact section is shown in FIG. 4. As is shown, a lead 39 is secured to a contact piece 36 of a metal (for instance brass) by means of soldering or caulking.

Designated at 37 is a metal member (for instance made of brass) into which the contact piece 36 is removably inserted to facilitate the replacement, and which is welded or bonded to the plate spring 34.

In FIG. 2, a hole 38 is formed in the shaft 22 within each case, through which holes the leads 39 are led into the upper portion of the shaft for connection to the lead 13 from the light receiving element within the tester. After the leads 39 are in position, the holes are sealed with an adhesive material.

Figure 3:
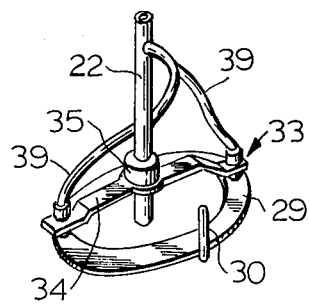
FIG. 3 is a fragmentary perspective view showing a metal ring.

FIG. 3 is a perspective view showing the relationship of the contact sections 33, a ring 29, lead 30 and plate spring 34. Leads 39 leading from opposite contacts are connected before insertion through the hole 38. Oil 41 is provided in each case to a level to cover the metal rings 29 and contact sections 33. Metal pieces 42 secure the contact means 14 by screws or other means to the bottom of the weather resistance tester. The shaft 5 of the sample rotating frame of the weather resistance tester is provided at its lower end with a flange 43, which is connected to the flange 23 on top of the rotating shaft 22. Thus while the light receiving element is rotated, photocurrent therefrom can be fed to the meter 16.

Figure 5:
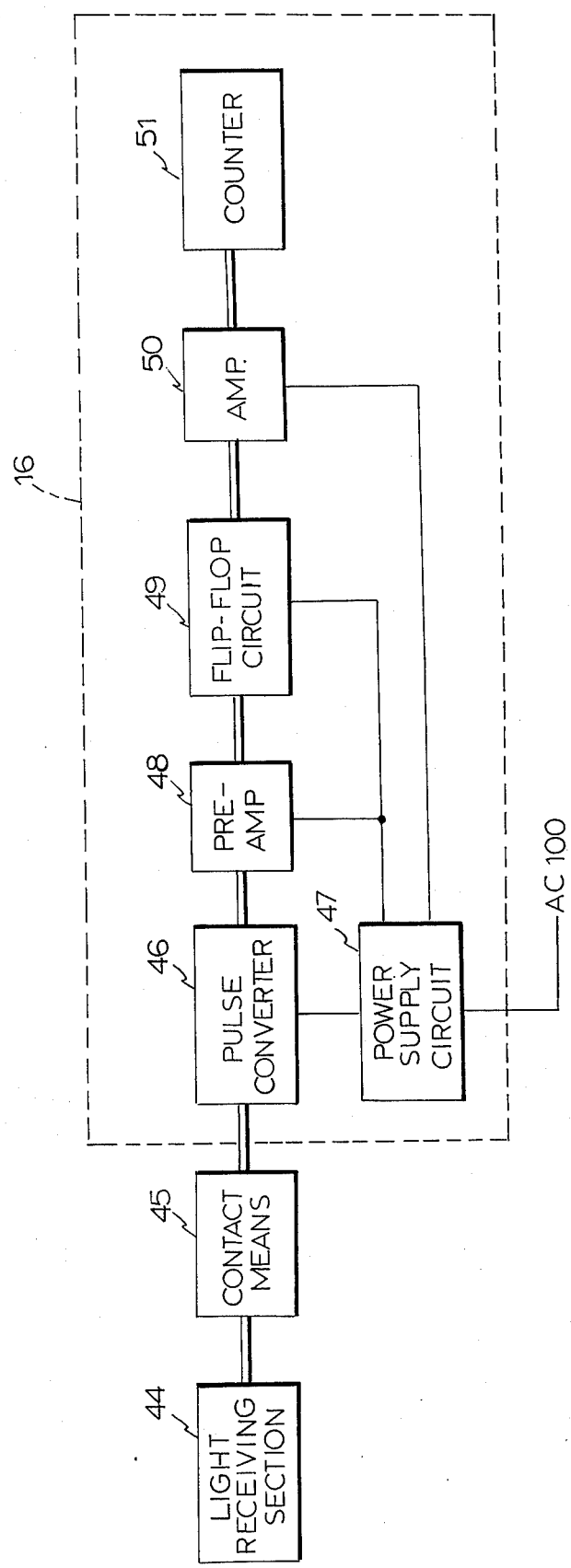

An example of the light energy measuring system using the contact means according to the invention will now be described in connection with FIG. 5.

A light receiving section 44 consisting of a filter and a photoelectric tube, i.e. element 12, converts light energy into corresponding electric current. The contact means according to the invention is shown schematically at 45 and is connected between light receiving section 44 and meter 16 shown enclosed within a dashed rectangle.

Designated at 46 within the meter is a pulse converter for converting current from the light receiving section 44 into a corresponding pulse signal, which is amplified through a preamplifier 48 and is then converted into a binary signal by a flip-flop circuit 49. The pulse output of the flip-flop circuit is amplified in an amplifier 50 and is then counted by counter 51. A power supply circuit 47 couples a power source to the individual circuit elements.

The energy received by the light receiving section 44 is counted as pulses by the counter 51 in proportion to its intensity. Thus, by calibrating the value of energy required to produce one count, the energy value can be determined from the total count.

The contact means according to the invention and that according to the prior art were tested to obtain comparative data as discussed hereinbelow.

As has been described above, where there is a reduction of the insulation resistance of the contact section, the count number is increased to thereby increase the measurement error because of the electric properties of the photoelectric tube. With an initial insulation resistance above 2,000 M$\omega$ the count number for energy from a carbon arc lamp is normal and is about 60 pulses per minute. However, with reduction of the resistance of the contact means, the count number increases, as shown below, even for the same energy from the arc lamp.

| RESISTANCE | COUNT NUMBER FOR ONE MINUTE |
| --- | --- |
| Above 2,000 M$\Omega$ | 60 |
| 200 M$\Omega$ | 70 |
| 20 M$\Omega$ | 150 |

Figure 6:
FIG. 6 is a graph showing the results of a test using the contact means according to the invention.

The contact means according to the invention maintains the initial resistance value substantially at 2,000 M$\omega$ for a long period of time, as shown in FIG. 6, which shows resistance plotted versus number of days of use.

Figure 7:
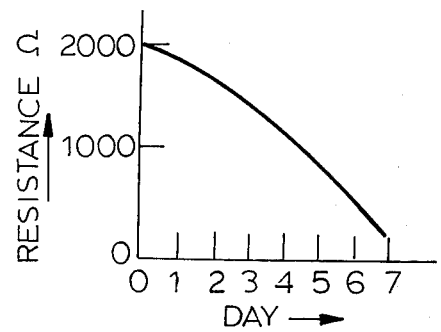
FIG. 7 is a graph showing results of a test using a prior art contact means.

On the other hand, with the prior art contact means, the resistance was reduced to 20 M$\omega$ in about seven days, as shown in FIG. 7.

As has been described above, the contact means according to the invention makes it possible to obtain accurate measurement of the light energy in the weather resistance tester for a long period of use.

WHAT IS CLAIMED IS:

1. In a weather resistance and solar radiation tester having a specimen rotating frame rotatable on a shaft around a light source and having a light receiving element on the specimen rotating frame having leads extending through the shaft and a meter for indicating the amount of light received by said light receiving element, improved contact means for electrically connecting the leads to the meter, said contact means comprising a rotating shaft connected to said shaft for the specimen rotating frame, upper and lower cases surrounding said rotating shaft and in which said rotating shaft is rotatably journaled and defining two separate compartments spaced along said rotating shaft and sealed from each other, said cases being of electrically insulating material, a metal ring fixed in the bottom of each case and a lead extending from each ring out through the respective case for connection to the meter, a plate spring in each compartment fixed to said rotating shaft, at least one contact piece on said plate spring in each compartment and in sliding contact with said metal rim therein and held in contact by said plate spring, one of said leads extending through said rotating shaft into one compartment and being electrically connected to the contact piece therein and the other of said leads extending through said rotating shaft and into the other compartment and being electrically connected to the contact piece therein, and an electrically insulating liquid in each compartment covering said rings and contact pieces therein, whereby deterioration of the resistance value of the contact means is avoided by elimination of the contamination due to contact wear.

2. The contact means as claimed in claim 1 wherein there are two contact pieces in each compartment, said plate spring extending diametrally from said rotating shaft and having a contact piece on each end thereof, and the lead extending into each compartment is branched with one branch extending to each contact piece.

3. The contact means as claimed in claim 1 in which each case is an open topped case, and said contact means further comprises a lid over the uppermost of the two cases, and packing means between the upper and lower cases and between said upper case said lid, said rotating shaft extending through the lid is in rotational relationship therewith, and sealing means between the lid and the rotating shaft and between the upper case and the rotating shaft.

4. Improved contact means for electrically connecting leads on a rotating member to leads on a fixed member, said contact means comprising a rotating shaft connected to the rotating member, upper and lower cases surrounding said rotating shaft and in which said rotating shaft is rotatably journaled and defining two separate compartments spaced along said rotating shaft and sealed from each other, said cases being of electrically insulating material, a metal ring fixed in the bottom of each case and a lead extending from each ring out through the respective case for connection to leads on a fixed member, a plate spring in each compartment fixed to said rotating shaft, at least one contact piece on said plate spring in each compartment and in sliding contact with said metal ring therein and held in contact by said plate spring, one of said leads extending through said rotating shaft into one compartment and being electrically connected to the contact piece therein and the other of said leads extending through said rotating shaft and into the other compartment and being electrically connected to the contact piece therein, and an electrically insulating liquid in each compartment covering said rings and contact pieces therein, whereby deterioration of the resistance value of the contact means is avoided by elimination of the contamination due to contact wear.

* * * * *